US00PP21131P2

(12) United States Plant Patent
Klemm et al.

(10) Patent No.: US PP21,131 P2
(45) Date of Patent: Jun. 29, 2010

(54) ***NEMESIA* PLANT NAMED 'KLENH08459'**

(50) Latin Name: *Nemesia hybrida*
Varietal Denomination: KLENH08459

(75) Inventors: Nils Klemm, Stuttgart (DE); Katinka Wilde, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/384,088

(22) Filed: Mar. 31, 2009

(51) Int. Cl.
*A01H 5/00* (2006.01)

(52) U.S. Cl. ..... Plt./458

(58) Field of Classification Search ..... Plt./458
See application file for complete search history.

*Primary Examiner*—Kent L Bell
(74) *Attorney, Agent, or Firm*—Jondle & Associates, P.C.

(57) ABSTRACT

A new cultivar of *Nemesia* named 'KLENH08459' particularly characterized by vibrant yellow flowers, and large, fully-opened flowers, is disclosed.

1 Drawing Sheet

Genus and species: *Nemesia hybrida.*
Variety denomination: 'KLENH08459'.

BACKGROUND OF THE NEW PLANT

The present invention comprises a new and distinct cultivar of *Nemesia*, botanically known as *Nemesia hybrida*, and hereinafter referred to by the cultivar name 'KLENH08459'. 'KLENH08459' originated from a controlled cross made in June 2004 in Stuttgart, Germany between the proprietary female *Nemesia* plant 'SB 1' (unpatented) and the proprietary male *Nemesia* plant 'W 076' (unpatented). A single plant selection was subsequently chosen for further evaluation and for asexual propagation.

The new cultivar was first propagated in September 2005 by vegetative cuttings in Stuttgart, Germany and has been asexually reproduced repeatedly by vegetative cuttings and in-vitro propagation in Stuttgart, Germany for about a three and one-half year period (about eight generations). 'KLENH08459' has been found to retain its distinctive characteristics through successive asexual propagations.

Plant Breeders Rights have not been applied for this cultivar. 'KLENH08459' has not been made publicly available more than one year prior to the filing date of the instant application.

SUMMARY OF THE INVENTION

The following are the most outstanding and distinguishing characteristics of this new cultivar when grown under normal commercial practices in a greenhouse in Stuttgart, Germany.

1. Vibrant yellow flowers; and
2. Large, fully-opened flowers.

DESCRIPTION OF THE PHOTOGRAPH

This new *Nemesia* plant is illustrated by the accompanying photograph which shows a close-up of the mature flowers, buds and foliage. The colors shown are as true as can be reasonably obtained by conventional photographic procedures. The photograph is of a plant about 18-weeks old and grown from rooted cuttings in 10.5 cm pots in a greenhouse (glasshouse) in Stuttgart, Germany in spring 2008 under conditions which approximate those generally used in commercial practice.

DESCRIPTION OF THE NEW CULTIVAR

The following detailed descriptions set forth the distinctive characteristics of 'KLENH08459'. The data which define these characteristics were collected from asexual reproductions carried out in Stuttgart, Germany. The plant history was taken on 18-week old plants in 10.5 cm pots that were pinched once after 10 weeks and grown in a greenhouse in spring 2008. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Scrophulariaceae.
- *Genus and species.*—*Nemesia hybrida.*
- *Common name.*—*Nemesia.*

Parentage:
- *Female parent.*—The proprietary female *Nemesia* plant 'SB 1' (unpatented).
- *Male parent.*—The proprietary male *Nemesia* plant 'W 076' (unpatented).

Plant:
- *Habit or form.*—Upright.
- *Vigor.*—Vigorous.
- *Height (measured from the top of the soil, including any flowers).*—About 35.0 cm.
- *Spread/width (horizontal plant diameter, including any flowers).*—About 30.0 cm.
- *Life cycle.*—Annual.
- *Time to produce a rooted cutting.*—3 to 4 weeks.
- *Time to produce a finished flowering plant.*—6 weeks.
- *Flowering season.*—Spring.
- *Root description.*—Filiform, pale-colored roots with root hairs.
- *Rooting habit.*—High root density and freely branching.
- *Temperature tolerances.*—5° C. to 35° C.

*Environmental conditions for plant growth and performance.*—Tolerates wind and rain and has good outdoor performance.

Branches:

*Type.*—More basal.
*Quantity per plant.*—About 8.
*Length.*—About 35.0 cm.
*Diameter.*—0.3 cm to 0.5 cm.
*Internode length.*—About 2.5 cm.
*Strength of branches.*—Fleshy, robust, strong.
*Shape of branches in cross-section.*—Square.
*Color.*—RHS 144A.
*Texture.*—Smooth.
*Stem anthocyanin.*—Absent.
*Branch pubescence.*—Absent.

Leaves:

*Arrangement.*—Opposite and sessile.
*Shape.*—Lanceolate.
*Apex.*—Cuspidate.
*Base.*—Obtuse.
*Margin.*—Serrate.
*Length.*—3.0 cm to 5.0 cm.
*Width.*—1.2 cm to 2.0 cm.
*Color.*—Upper surface: RHS 138A. Lower surface: RHS 138B.
*Variegation.*—Absent.
*Surface texture* (*both surfaces*).—Smooth.
*Venation pattern.*—Pinnate.
*Venation color.*—Upper surface: RHS 138A for immature leaves. Lower surface: RHS 138B for immature leaves.
*Petioles.*—Absent.

Flower bud:

*Quantity per inflorescence.*—2 to 5.
*Shape.*—Obovate.
*Surface texture.*—Smooth.
*Diameter.*—0.3 cm to 0.5 cm.
*Length.*—0.5 cm to 1.8 cm.
*Color* (*at tight bud*).—RHS 149D.

Inflorescence:

*Inflorescence type.*—Raceme.
*Lastingness of inflorescence on the plant.*—About 7 days.
*Quantity of flowers per inflorescence.*—2 to 6.
*Inflorescence length.*—About 14.0 cm.
*Inflorescence diameter.*—About 2.0 cm not including the flowers and about 3.5 cm including the flowers.
*Flower diameter.*—About 2.0 cm.
*Flower depth* (*including nectar spur*).—About 1.0 cm.
*Nectar spur length.*—About 0.4 cm.
*Fragrance.*—Yes, typical of *Nemesia.*
*Self-cleaning or persistent.*—Self-cleaning.

Petals:

*Arrangement and shape.*—Zygomorphic; flowers are arranged on terminal racemes; four petals are fused at the base and the fifth lower petal is modified into a large lip.
*Quantity per flower.*—5.
*Length* (*both the upper and lower lips*).—About 2.8 cm.
*Width.*—Upper lip: About 2.0 cm. Lower lip: About 2.0 cm.
*Apex.*—Lobate/obtuse.
*Margin.*—Entire.
*Color.*—Upper lip: Upper or forward facing surface: RHS 12A with RHS 86A eyes. Lower or rear facing surface: RHS 12A. Lower lip: Upper or forward facing surface: RHS 12A with RHS 86A eyes. Lower or rear facing surface: RHS 12A.
*Texture* (*both surfaces of upper and lower lips*).—Smooth, no pubescence.
*Nectar spur color.*—RHS 10D.
*Nectar guide color.*—RHS 17A.
*Spur length.*—About 0.4 cm.
*Spur diameter at the base.*—About 0.6 cm.
*Spur diameter at the tip.*—About 0.2 cm.
*Spur texture.*—Smooth.

Calyx:

Shape and arrangement.—Star-shaped with 5 sepals fused at the base.
*Sepals.*—Quantity: 5. Apex: Cuspidate. Base: Fused. Margin: Entire. Color (both surfaces): RHS 141C. Length: About 0.7 cm. Diameter: About 0.7 cm. Surface texture (both surfaces): Pubescent.

Pedicel:

*Length.*—About 1.0 cm.
*Diameter.*—About 0.1 cm.
*Color.*—RHS 141C.
*Surface texture.*—Pubescent.

Peduncle:

*Length.*—About 4.5 cm.
*Diameter.*—About 0.2 cm.
*Color.*—RHS 141C.
*Surface texture.*—Smooth.

Reproductive organs:

*Stamens.*—Number per flower: 4. Length: About 0.4 cm. Filament color: RHS 156D. Filament length: About 0.3 cm. Filament diameter: About 0.1 cm. Anther color: RHS 14C. Anther length: About 0.1 cm. Pollen amount: Moderate. Pollen color: RHS 14C.
*Pistil.*—Pistil number: 1. Pistil length: About 0.3 cm. Stigma color: RHS 157D. Stigma length: Not distinguishable from style. Style length: About 0.1 cm. Style color: RHS 157D.
*Ovary.*—Shape: Ovate. Color: RHS 143C.

Fruit and seed set: None observed.

Disease and insect resistance: None observed.

COMPARISON WITH PARENTAL AND COMMERCIAL CULTIVARS

'KLENH08459' differs from the proprietary female *Nemesia* plant 'SB 1' (unpatented) in that 'KLENH08459' has vibrant yellow flowers, while 'SB 1' has purple-pink flowers.

'KLENH08459' differs from the proprietary male *Nemesia* plant 'W 076' (unpatented) in that 'KLENH08459' has large, vibrant yellow flowers, while 'W 076' has small, dark blue flowers.

'KLENH08459' differs from the commercial comparison variety 'KLENH06157' (unpatented) in that 'KLENH08459' has vibrant yellow flowers, while 'KLENH06157' has pale yellow flowers. Additionally, 'KLENH08459' has flowers that open fully, while 'KLENH06157' has flowers that are crimped.

I claim:

1. A new and distinct cultivar of *Nemesia* plant named 'KLENH08459' as shown and described herein.

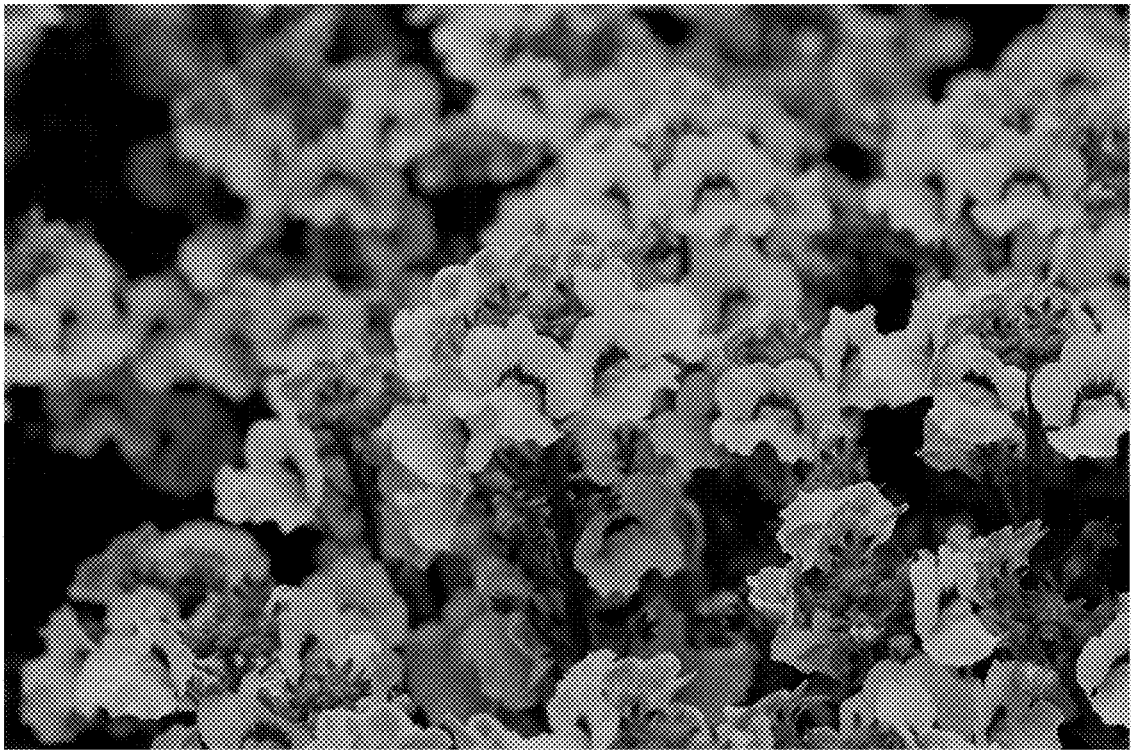

* * * * *